United States Patent
Daly et al.

(10) Patent No.: US 9,758,760 B2
(45) Date of Patent: *Sep. 12, 2017

(54) COMPOSITIONS CONTAINING AMINO ACIDS, PHOSPHATE AND MANGANESE AND THEIR USES

(71) Applicant: The Henry M. Jackson Foundation for the Advancement of Military Medicine, Inc., Bethesda, MD (US)

(72) Inventors: Michael J. Daly, Washington, DC (US); Elena K. Gaidamakova, Gaithersburg, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/962,596

(22) Filed: Dec. 8, 2015

(65) Prior Publication Data

US 2016/0222343 A1 Aug. 4, 2016

Related U.S. Application Data

(63) Continuation of application No. 13/643,794, filed as application No. PCT/US2011/034484 on Apr. 29, 2011, now Pat. No. 9,234,168.

(60) Provisional application No. 61/329,381, filed on Apr. 29, 2010.

(51) Int. Cl.
| | |
|---|---|
| C12N 1/20 | (2006.01) |
| A61K 31/7072 | (2006.01) |
| A61K 39/085 | (2006.01) |
| C12N 7/00 | (2006.01) |
| A61K 31/7076 | (2006.01) |
| A61K 39/02 | (2006.01) |
| A61K 39/12 | (2006.01) |
| A61K 39/108 | (2006.01) |
| A61K 39/00 | (2006.01) |

(52) U.S. Cl.
CPC ............ *C12N 1/20* (2013.01); *A61K 31/7072* (2013.01); *A61K 31/7076* (2013.01); *A61K 39/02* (2013.01); *A61K 39/0258* (2013.01); *A61K 39/085* (2013.01); *A61K 39/12* (2013.01); *C12N 7/00* (2013.01); *A61K 2039/521* (2013.01); *A61K 2039/522* (2013.01); *A61K 2039/5252* (2013.01); *C12N 2710/00061* (2013.01); *C12N 2795/10334* (2013.01)

(58) Field of Classification Search
None
See application file for complete search history.

(56) References Cited

U.S. PATENT DOCUMENTS

| | | | |
|---|---|---|---|
| 4,897,346 A | 1/1990 | Gawronski | |
| 4,959,211 A | 9/1990 | Lombardo et al. | |
| 5,066,500 A | 11/1991 | Gil et al. | |
| 5,407,669 A | 4/1995 | Lindstrom | |
| 5,536,645 A | 7/1996 | Jay | |
| 6,187,572 B1 | 2/2001 | Platz et al. | |
| 9,234,168 B2 * | 1/2016 | Daly ................ | A61K 31/7072 |
| 2003/0143707 A1 | 7/2003 | Narumi et al. | |
| 2004/0029129 A1 | 2/2004 | Wang et al. | |
| 2006/0264357 A1 | 11/2006 | Zikria et al. | |
| 2007/0189992 A1 | 8/2007 | Gupta | |
| 2009/0269370 A1 | 10/2009 | Cohen et al. | |
| 2011/0177111 A1 | 7/2011 | Shirtliff et al. | |
| 2011/0183021 A1 * | 7/2011 | Daly ................ | A61K 31/7076 424/780 |

FOREIGN PATENT DOCUMENTS

| | | |
|---|---|---|
| EP | 0263684 | 4/1988 |
| JP | 2007-176879 | 7/2007 |
| WO | 89/03838 | 5/1989 |
| WO | 92/13561 | 8/1992 |
| WO | 96/04923 | 2/1996 |
| WO | 02/053138 | 7/2002 |
| WO | 2004/056388 | 8/2004 |
| WO | 2009/020480 | 2/2009 |
| WO | 2009/045655 | 4/2009 |

OTHER PUBLICATIONS

Datta et al., "Vaccination with irradiated Listeria induces protective T cell immunity," Immunity, 25(1):143-152 (2006).
Daly et al., "Death by protein damage in irradiated cells," DNA Repair, 11:12-21 (2012).
"Polyvalent vaccine production by radiation inactivation of microorganisms," Ed-Hanekom Professor Willem; Kollmann Assist Prof Tobias R; Levy Assist Prof Ofer, Vaccine, 4(4):272-273 (1986).
Accession No. 2005-311366, Database WPI, Thomson, Chung et al., "Extract of hydrophobic substance being in cell membrane of Deinococcus radiodurans for skin protection and composition for external use containing the same" (2004).

(Continued)

*Primary Examiner* — Gary Nickol
*Assistant Examiner* — Mary Lyons
(74) *Attorney, Agent, or Firm* — Morgan, Lewis & Bockius LLP

(57) ABSTRACT

The invention provides methods of producing vaccines directed against microorganisms, with the methods comprising culturing, harvesting and/or suspending the microorganism in the presence of a radiation-protective composition and irradiating the bacteria or viruses with a dose of radiation sufficient to render the microorganism replication-deficient and/or non-infective. The radiation-protective compositions used in the methods of the present invention comprise at least one nucleoside, at least one antioxidant and at least one small peptide. The invention also provides methods of rendering bacteria in culture resistant to ionizing radiation (IR), with these methods comprising culturing the bacteria in the presence of a radiation-protective composition.

39 Claims, 10 Drawing Sheets

(56) References Cited

OTHER PUBLICATIONS

Accession No. 2007-703653, Database WPI, Week 200766, Thomson Scientific, London, GB (2007).

Bruce, "Extraction of the radioresistant factor of Micrococcus radiodurans," Radiation Research, 22:155-164 (1964).

Daly et al., "Accumulation of Mn(II) in Deinococcus radiodurans facilitates gamma-radiation resistance," Science, 306 (5698)1025-1028 (2004).

Daly et al., "Small-molecule antioxidant proteome-shields in Deinococcus radiodurans," PLoS One, 5(9): e12570 (2010).

Ding et al., "Identification of protein components and quantitative immunoassay for SEC2 in staphylococcin injection," J. Pharm. Biomed. Anal., 50(1):79-85 (2009).

Gaidamakova et al., "Preserving immunogenicity of lethally irradiated viral and bacterial vaccine epitopes using a radio-protective Mn2+-Peptide complex from Deinococcus," Cell Host & Microbe, 12(1):117-124 (2012).

Goldstein et al., Radioprotection in *E. coli* by an agent from M. radioduransInt. J. Radial Biol. Relat. Stud. Phys. Chem. Med., 34(4):375-380 (1978).

Krisko et al., "Protein damage and death by radiation in *Escherichia coli* and Deinococcus radiodurans," Proc Natl Acad Sci U S A., 107(32):14373-14377 (2010).

Lee et al., "A manganese porphyrin complex is a novel radiation protector," Free Radical Biology & Medicine, 37 (2):272-283 (2004).

Hosseinimehr, "Potential Utility of Radioprotective Agents in the Practice of Nuclear Medicine," Cancer Biotherapy & Radiopharmaceuticals, 24(6): 723-731 (2009).

Daly et al., "Protein oxidation implicated as the primary determinant of bacterial radioresistance," PLoS Biol., 5:e92 (2007).

International Search Report issued in related International Patent Application No. PCT/US2008/073479, dated Aug. 18, 2009.

International Search Report issued in related International Patent Application No. PCT/US2011/034484, dated Jan. 11, 2012.

International Search Report issued in related International Patent Application No. PCT/US2012/062998, dated Apr. 18, 2013.

Guo et al., "Protein tolerance to random amino acid change," Proc Natl Acad Sci USA, 101(25):9205-9210 (2004).

Ogata et al., "Mortality reduction in mice administered a single abundant dose of zinc, manganese or magnesium after Irradiation by gamma-rays at sublethal doses," Radioisotopes, 39(12):573-576 (1990) (Article in Japanese with English Abstract).

Ohta et al., "Studies on chemical protectors against radiation. XXX. Radioprotective substances of cnidii rhizoma," Yakugaku Zasshi, Journal of the Pharmaceutical Society of Japan,110(10):746-754 (1990) (Article in Japanese with English Abstract).

* cited by examiner

| GROUP | DAY 1 | DAY 13 | DAY 28 |
|---|---|---|---|
| IRS + PBS | IRRADIATED, UNPROTECTED MRSA ($10^8$ CFUs) IN PBS | IRRADIATED, UNPROTECTED MRSA ($10^8$ CFUs) IN PBS | LIVE MRSA ($10^7$ CFUs) IN PBS + CYTODEX BEADS |
| IRS_CFA | IRRADIATED, UNPROTECTED MRSA ($10^9$ CFUs) IN 1mg/mL CFA | IRRADIATED, UNPROTECTED MRSA ($10^9$ CFUs) IN 1mg/mL CFA | LIVE MRSA ($10^7$ CFUs) IN PBS + CYTODEX BEADS |
| HK + PBS | HEAT KILLED MRSA ($10^8$ CFUs) IN PBS | HEAT KILLED MRSA ($10^8$ CFUs) IN PBS | LIVE MRSA ($10^7$ CFUs) IN PBS + CYTODEX BEADS |
| LIVE | LIVE MRSA ($10^7$ CFUs) IN PBS + CYTODEX BEADS | LIVE MRSA ($10^7$ CFUs) IN PBS + CYTODEX BEADS | LIVE MRSA ($10^7$ CFUs) IN PBS + CYTODEX BEADS |
| HK + CFA | HEAT KILLED MRSA ($10^8$ CFUs) IN 1mg/mL CFA | HEAT KILLED MRSA ($10^8$ CFUs) IN 1mg/mL CFA | LIVE MRSA ($10^7$ CFUs) IN PBS + CYTODEX BEADS |
| DPM IRS + PBS | PEPTIDE PROTECTED, IRRADIATED, MRSA ($10^9$ CFUs) IN PBS | PEPTIDE PROTECTED, IRRADIATED, MRSA ($10^9$ CFUs) IN PBS | LIVE MRSA ($10^7$ CFUs) IN PBS + CYTODEX BEADS |
| DPM IRS + CFA | PEPTIDE PROTECTED, IRRADIATED, MRSA ($10^8$ CFUs) IN 1mg/mL CFA | PEPTIDE PROTECTED, IRRADIATED, MRSA ($10^8$ CFUs) IN 1mg/mL CFA | LIVE MRSA ($10^7$ CFUs) IN PBS + CYTODEX BEADS |
| NAIVE | NOTHING | NOTHING | LIVE MRSA ($10^7$ CFUs) IN PBS + CYTODEX BEADS |

FIG. 6

COMPOSITIONS CONTAINING AMINO ACIDS, PHOSPHATE AND MANGANESE AND THEIR USES

GOVERNMENT SUPPORT

This invention was made with government support under DE-FG02-04ER63918 and FA9550-07-1-0218 awarded by Department of Energy and Air Force Office of Scientific Research, respectively. The government has certain rights in the invention.

SEQUENCE LISTING SUBMISSION VIA EFS-WEB

A computer readable text file, entitled "044508-5018-05-SequenceListing.txt" created on or about Nov. 19, 2015, with a file size of about 0.7 kb contains the sequence listing for this application and is hereby incorporated by reference in its entirety.

BACKGROUND OF THE INVENTION

Field of Invention

The invention provides methods of producing vaccines directed against microorganisms, with the methods comprising culturing, harvesting and/or suspending the microorganism in the presence of a radiation-protective composition and irradiating the microorganism with a dose of radiation sufficient to render the microorganism replication-deficient. The radiation-protective compositions used in the methods of the present invention comprise at least one decapeptide in a mixture of manganese-phosphate or manganese-bicarbonate buffer. The invention also provides methods of rendering a bacteria in culture resistant to ionizing radiation (IR), with these methods comprising culturing the bacteria in the presence of a radiation-protective composition.

Background of the Invention

The extremely radiation-resistant family Deinococcaceae is comprised of greater than twenty distinct species that can survive acute exposures to ionizing radiation (IR) (10 kGy), ultraviolet light (UV) (1 kJ/m$^2$), and desiccation (years); and can grow under chronic IR (60 Gy/hour). In particular, *Deinococcus radiodurans* is an extremely ionizing radiation (IR) resistant bacterium that can survive exposures to gamma-radiation that exceed by a factor of one thousand the doses which are cytotoxic and lethal to mammalian cells For extremely resistant bacteria, such as e.g., *D. radiodurans*, survival following high-doses of IR has been attributed to protection of proteins from oxidation during irradiation, with the result that enzymic repair systems survive and function with far greater efficiency during recovery than in sensitive bacteria, where cellular proteins are highly susceptible to carbonylation. In a report published in Science magazine (Daly et al. (2004), Accumulation of Mn(II) in *Deinococcus radiodurans* facilitates gamma-radiation resistance, Science 306: 925-1084), intracellular manganese(II) was implicated in facilitating radiation resistance by protecting proteins, but not DNA, during exposure to ionizing radiation; and in a second report published in PLoS Biology (Daly et al. (2007) Protein oxidation implicated as the primary determinant of bacterial radioresistance, PLoS Biology 5(4) e92), radiation resistance was positively correlated to protein protection during irradiation, mediated by a non-enzymic mechanism.

Unlike *D. radiodurans*, most proteins are not radiation-resistant. Similarly, most cells, whether in eukaryotes, prokaryotes or mammals (e.g. humans) are also not radiation resistant. As such, exposure to radiation is quite damaging to protein structure and/or function. For example, ionizing radiation has been shown to induce (cause) cancer in many different species of animals and in almost all parts of the human body.

In humans, significant overexposure to radiation can result in radiation poisoning, also called "radiation sickness" or a "creeping dose". The term is generally used to refer to acute problems caused by a large dosage of radiation in a short period, though this also has occurred with long term exposure to low level radiation. The clinical name for "radiation sickness" is acute radiation syndrome as described by the CDC. A chronic radiation syndrome does exist but is very uncommon; this has been observed among workers in early radium source production sites and in the early days of the Soviet nuclear program. A short exposure can result in acute radiation syndrome; chronic radiation syndrome requires a prolonged high level of exposure.

Humans routinely encounter radiation in daily life, including radiation from electronic equipment and cell phones as well as natural background radiation. Individuals that are in close proximity of radioactive elements such as e.g. employees at a nuclear plant or members of the armed forces are particularly likely to encounter higher doses of radiation. Additionally, radiation is used in diagnostic tests such as X-rays and radiation therapy to treat cancers.

There are currently very few radioprotectors suitable for treating humans, and those which exist (e.g., amifostine) are cytotoxic and have serious side effects (e.g., loss of consciousness, fast or irregular breathing, itching, nausea and vomiting).

Given the great exposure to radiation, there is a significant need for radioprotectors that are non-toxic, preserve protein function, and in particular are suitable for human use.

SUMMARY OF THE INVENTION

The invention provides methods of producing vaccines directed against microorganisms, with the methods comprising culturing, harvesting and/or suspending the microorganism in the presence of a radiation-protective composition and irradiating the microorganism with a dose of radiation sufficient to render the microorganism replication-deficient. The radiation-protective compositions used in vaccine preparation methods of the present invention comprise at least one decapeptide in a manganese-containing buffer.

The invention also provides methods of rendering a bacteria in culture resistant to ionizing radiation (IR), with these methods comprising culturing the bacteria in the presence of a radiation-protective composition. The radiation-protective compositions used in IR-resistant methods of the present invention comprise at least one nucleoside, phosphate, at least one antioxidant and dimethyl sulfoxide (DMSO).

BRIEF DESCRIPTION OF THE DRAWINGS

(FIG. 4A) Cytosolic distribution and concentration of amino acids in *D. radiodurans*: "No-IR," non-irradiated control cells held in 25 mM potassium phosphate buffer, pH 7.4 on ice, then washed and held in 25 mM phosphate buffer, pH 7.4 (32° C.) for 0 or 30 min. "+IR," cells irradiated to 7 kGy in 25 mM phosphate buffer, pH 7.4 on ice, then washed and held in 25 mM phosphate buffer, pH 7.4 (32° C.) for 0 or 30 min. Cells were harvested, resuspended in 20% TCA, and lysed. Aliquots of neutralized supernatant were analyzed for free amino acid and peptide-derived amino acid content. (FIG. 4B) Radioprotection of BamHI by the decapeptide (H-Asp-Glu-His-Gly-Thr-Ala-Val-Met-Leu-Lys-OH; 1261 Da). (FIG. 4C) Radioprotection of glutamine synthetase (GS) by $Mn^{2+}$ and leucine (Leu), uridine (U), or the decapeptide (DP) in potassium phosphate buffer (PiB), pH 7.4 or sodium bicarbonate buffer ($HCO_3$), pH 7.4.

DETAILED DESCRIPTION

Figure 1:
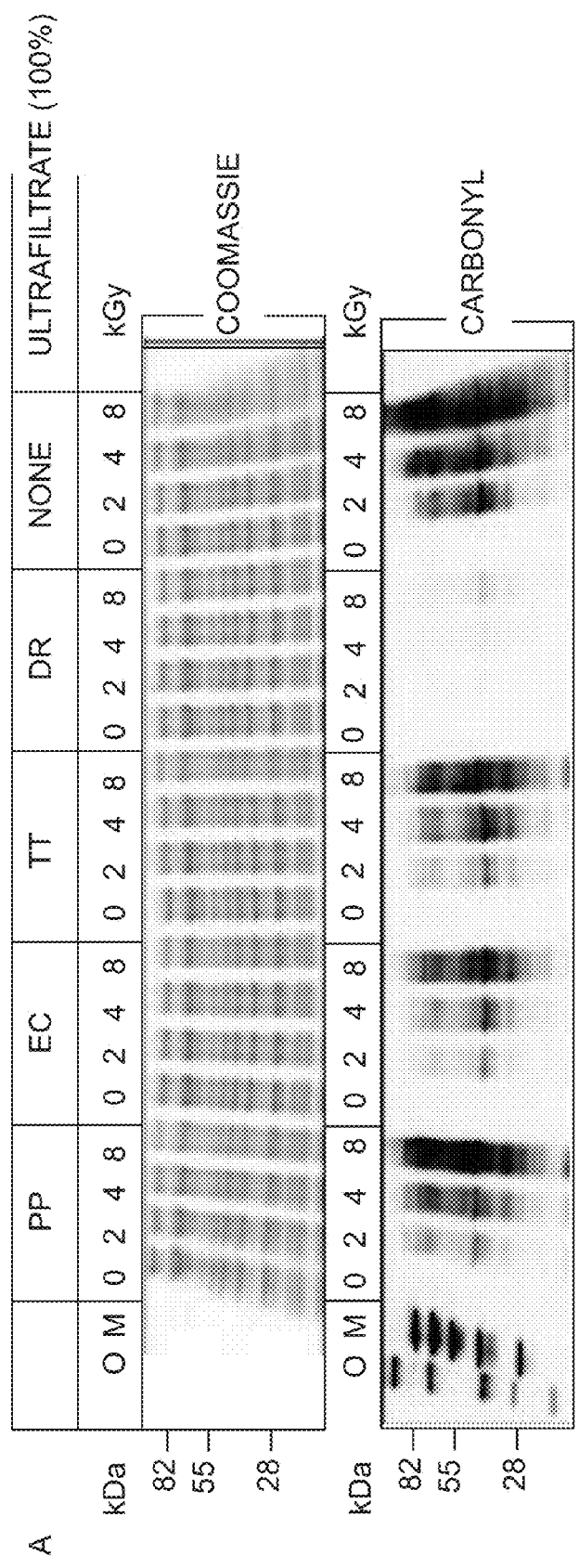
FIG. 1 shows that compounds in *D. radiodurans* ultrafiltrates protect proteins but compounds ultrafiltrates from in *Pseudonomas putida* (PP), *Escherichia coli* (EC), and *Thermus thermophilus* (TT) do not. Protein-free, ultra-filtrated *D. radiodurans* (DR) cell extract prevents ionizing radiation (IR)-induced protein oxidation in vitro, but extracts from the radiation sensitive bacteria *Pseudomonas putida* (PP), *Escherichia coli* (EC), and *Thermus thermophilus* (TT) did not. Purified *E. coli* proteins were incubated in PP-, EC-, TT-, or DR-ultra-filtrated extract during irradiation, and subjected to a protein carbonyl assay. Coomassie-stained polyacrylamide denaturing gel; Carbonyl Western blot, revealing protein oxidation and protection (no signal).
Figure 2A:
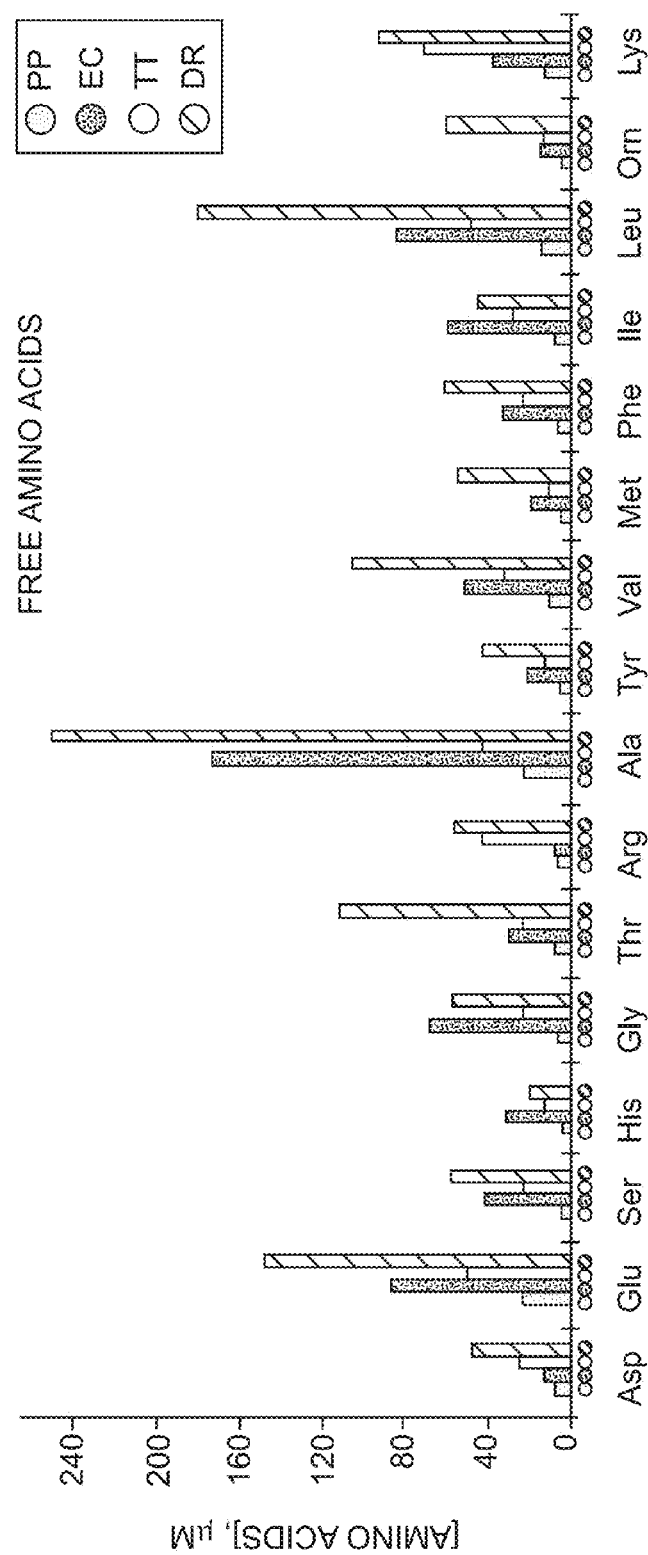
FIGS. 2A and 2B depict the composition of *Deinococcaceae radiodurans* (DR) ultrafiltrate in comparison to ultrafiltrate from *Pseudomonas putida* (PP), *Escherichia coli* (EC) and *Thermus thermophilus* (TT).
Figure 2B:
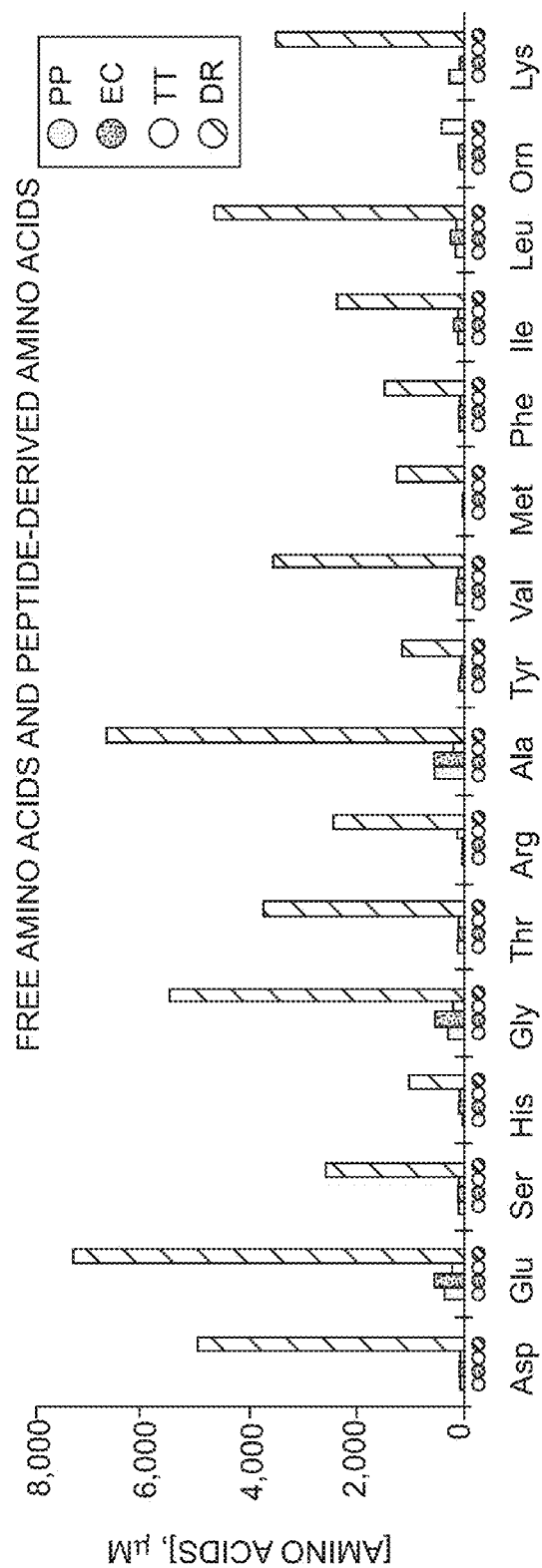
Figure 3:
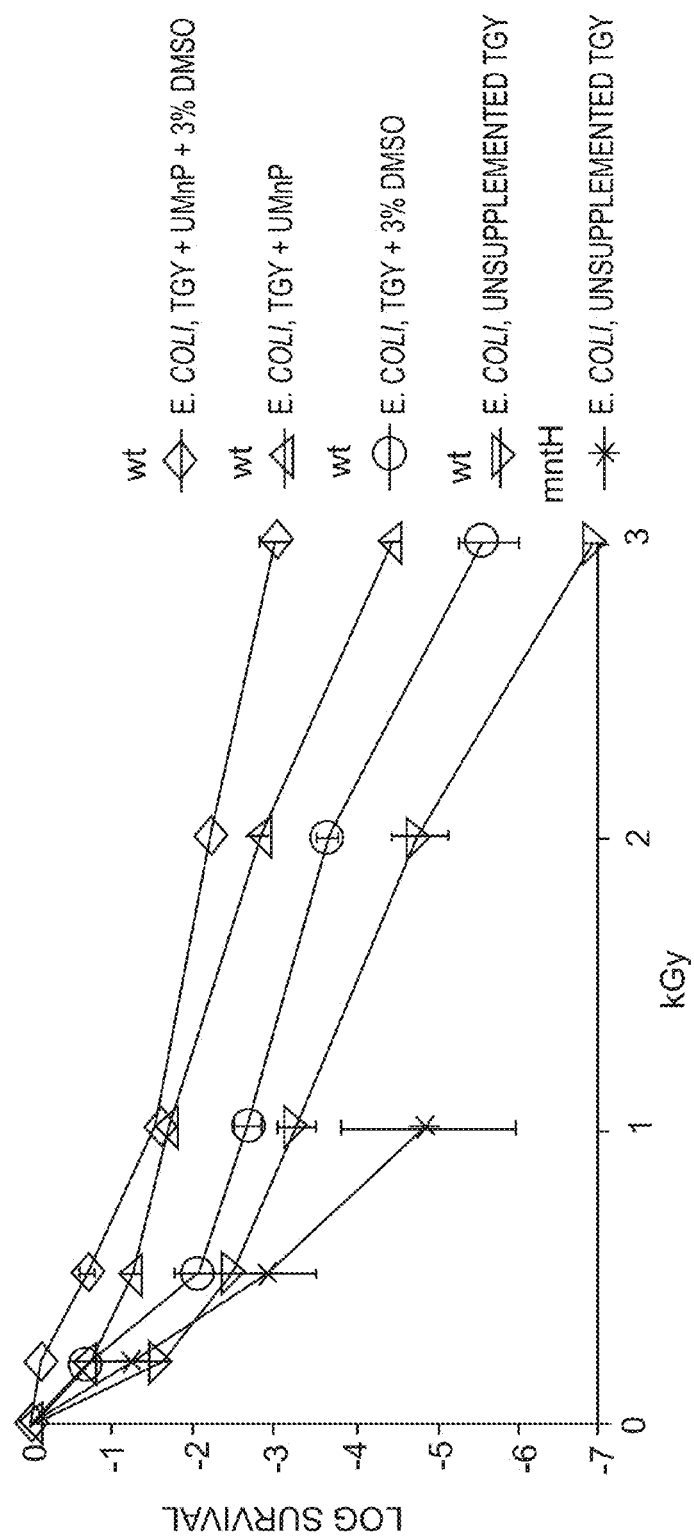
FIG. 3 depicts the survival curves of *E. coli* exposed to acute IR and grown in the presence of various supplements: TGY, standard peptide-rich growth medium; DMSO, dimethyl sulfoxide; UMnP, 3 mM uridine/1 μM $Mn^{2+}$/13 mM PiB (phosphate buffer).
Figure 4A:
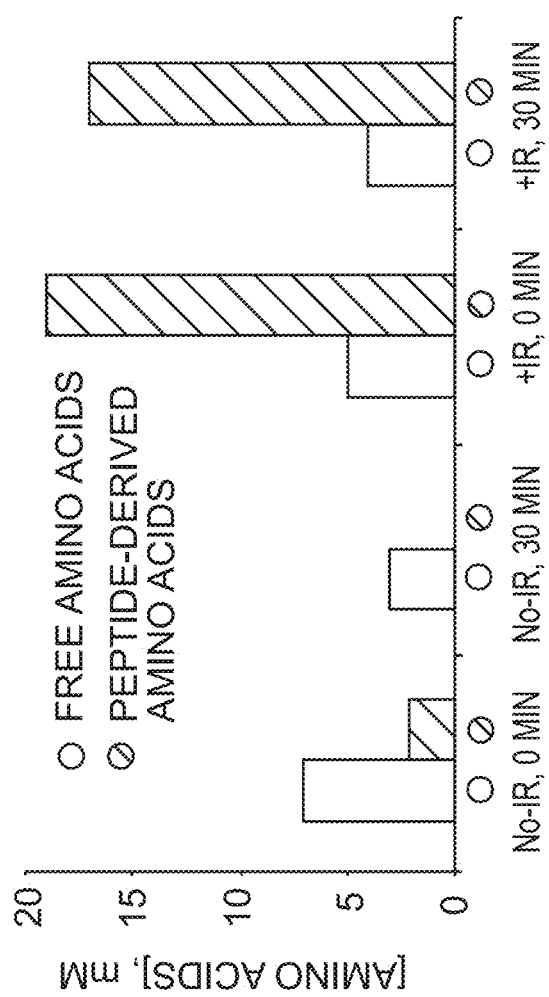
FIGS. 4A-4C depict the role of peptides in resistance to ionizing radiation.
Figure 4B:
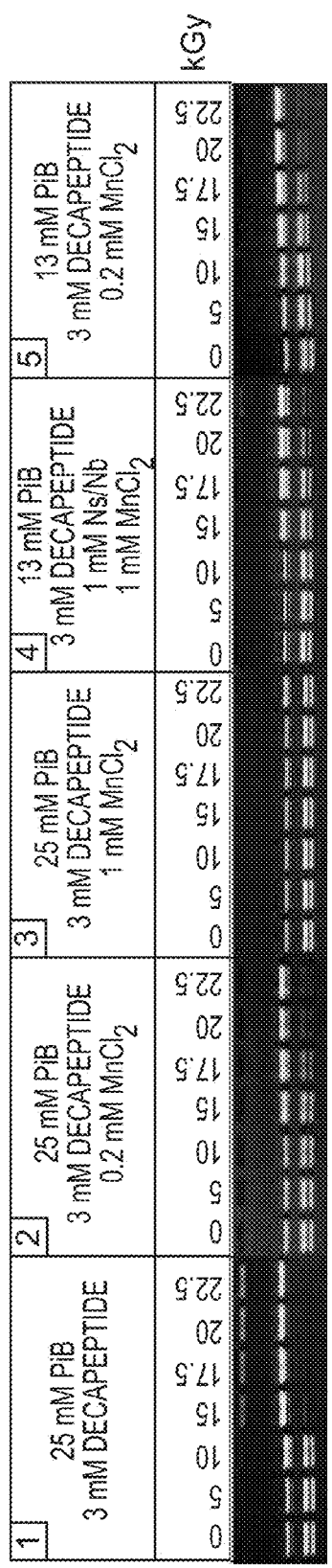
Figure 4C:
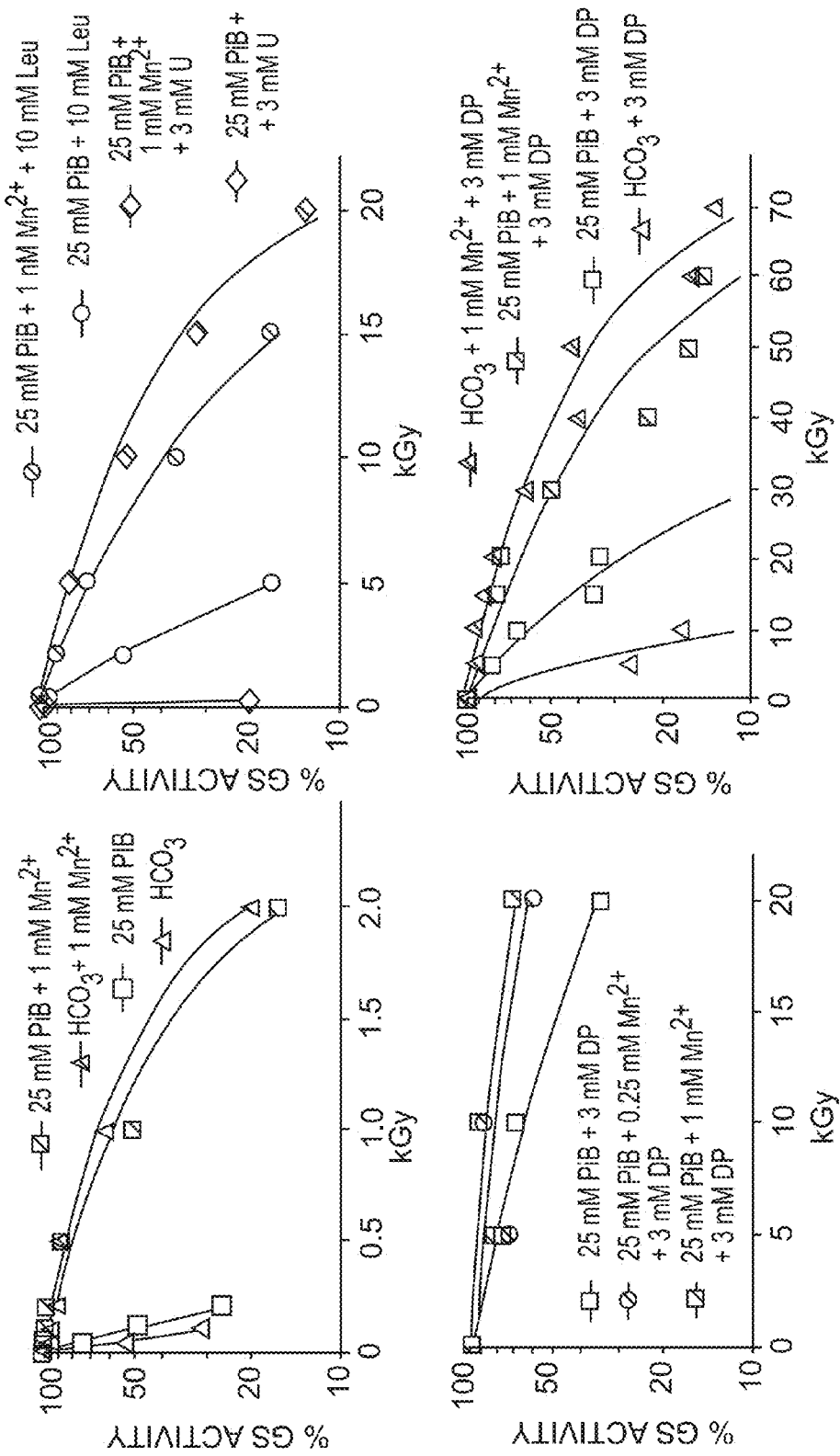

The inventors have studied the radio-resistance of *D. radiodurans* and prepared ultra-purified, protein free-cell extracts that exhibit radioprotective properties. Thus, the invention is based in part on the discovery of radioprotective components of *D. radiodurans* cell free extract and artificial compositions containing such components.

In particular, applicants have shown that *D. radiodurans* ultra-purified and protein-free cell extracts are extremely radioprotective of proteins exposed to gamma-radiation. Adenosine, uridine and peptides are accumulated in *D. radiodurans* ultrafiltrate at higher concentrations than in ultrafiltrates of radiation sensitive bacteria. In vitro, at doses >10,000 Gy, nucleosides were shown to be highly protective of proteins, preventing ionizing radiation (IR)-induced protein carbonylation and preserve the function enzymes in the presence of Mn(II). A radioprotective composition of adenosine, manganese, peptides and phosphate has been developed. Surprisingly, *D. radiodurans* extracts have been shown to be potent radioprotectors for cultured human T-cells with greater potency than other well-established radioprotective compounds.

The present invention provides for radioprotective compositions either synthetic or derived from *D. radiodurans* (DR) and methods of uses of these compositions to protect proteins and/or cells from radiation damage. These compositions are useful to prevent radiation damage in compositions as well as in subjects such as humans or in cell cultures. The composition of the present invention comprise manganese and at least one antioxidant peptide, or they comprise manganese and a collection of individual amino acids. In additional embodiments, the composition may also comprise at least one nucleoside. As used herein, the term "radioprotective composition" or "radiation protective composition" can mean either a DR ultrafiltrate extract prepared according to methods described herein, or it can mean a synthetic composition comprising manganese and at least one antioxidant peptide or a collection of individual amino acids. If a DR ultrafiltrate extract is used, this extract can be supplemented with any of the compounds described and disclosed herein. For example, the DR ultrafiltrate may be prepared according to the methods disclosed herein, and additional Me or peptides, for example, may be added to the extract.

The radioprotective compositions may further contain leucine, alanine, and/or valine. Leucine is strongly implicated in scavenging hydrogen peroxide in the presence of Mn(II), and may be components of larger intracellular complexes that include uridine and adenosine. Strong in vitro evidence indicates a synergistic effect between adenosine and manganese and phosphate. The stoichiometry of adenosine and manganese and phosphate or bicarbonate buffers may be optimized for an apoptosis assay.

Applicants have shown that adenosine alone and Mn(II) alone are radioprotective in vivo for a mammalian cell line and for a bacterial cell culture.

Although not being bound by any particular theory, it is believed that compositions comprising purine nucleosides (e.g. adenosine), pyrimidine nucleosides (e.g., uridine) and a peptide antioxidant (e.g. manganese-peptide) act as radioprotectants by shielding a proteins' active site and surface. The purine nucleoside e.g. adenosine (and optionally combined with the pyrimidine nucleoside uridine, and peptides) mediates its radioprotective effects upon accumulation within a cell, which inhibits radiation-induced protein oxidation, and in the presence of Mn(II) preserves enzyme function. Adenosine is thought to protect proteins, and therefore scavenge a subset of ROS.

Furthermore, without being bound by any particular theory, it is believed that under aerobic or anaerobic irradiation conditions, superoxide can build up in cells during irradiation because superoxide does not readily cross membranes. Although superoxide does not react with DNA, superoxide will damage and inactivate enzymes with exposed 2Fe-2S or 4Fe-4S clusters, releasing Fe(II) and also damage certain exposed amino acids such as, but not limited to, cysteine. The problem with iron in a cell, when it is unbound and "free", is that it causes Fenton reactions in the presence of hydrogen peroxide, generating hydroxyl radicals. Therefore, conditions which liberate bound Fe(II) are extremely dangerous, not only because of the generation of hydroxyl radicals, but because the loss of Fe from Fe-dependent enzymes leads to the failure of the biochemical pathways within which they operate. The methods of the instant application optimally protect against these dangerous conditions.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods, and materials are described.

As used herein, "a" or "an" means at least one, unless clearly indicated otherwise. The term "about," unless otherwise indicated, refers to a value that is no more than 10% above or below the value being modified by the term. For example, the term "about 5% (w/w)" means a range of from 4.5% (w/w) to 5.5% (w/w).

This invention provides for methods of preserving protein function or protein immunogenicity comprising contacting a protein with a composition of the present invention. One embodiment of the invention is a method preserving protein function when the protein is exposed to the extreme conditions of radiation such as e.g. gamma radiation. In another embodiment of the invention, the method preserves protein function during desiccation.

The methods of preserving protein function provide radioprotection when the protein is exposed to high dose of radiation such as doses in excess of 10 kGy, e.g., 17.5 kGy.

In another embodiment, the invention provides for methods of protecting protein function or protein immunogenicity in a cell culture or virus preparation comprising culturing, harvesting and/or suspending the cells with any of the radio-protective compositions described herein. The virus preparation may be for DNA or RNA genomes, single-stranded or double-stranded. The cell culture may be prokaryotic or eukaryotic. In one embodiment, the cell culture is bacterial. In another embodiment the cell culture is mammalian. In yet another embodiment, the cell culture is a culture for the purpose of propagating viruses.

Any nucleoside, if present, may be used in the radiation protective compositions. Suitable nucleosides include, but are not limited to, adenosine, uridine, β-pseudouridine, inosine, and mixtures thereof. In addition, analogues of nucleosides containing two carbonyl oxygen groups (C=O) separated by one (N3)H group can also be used. In one embodiment, the nucleoside is adenosine or uridine. In one embodiment, the composition contains adenosine. In other embodiment of the invention, the composition contains uridine. The amount of nucleoside in the composition varies on its use. Those of skill in the art will be able to determine the suitable amount. In some embodiments of the invention, the amount of nucleoside ranges from about 0.01 mM to about 15 mM, from about 0.1 mM to about 1 mM, from about 1 mM to about 10 mM, from about 1 mM about 15 mM. In one embodiment, the concentration of one or more nucleosides comprises about 1 mM to about 15 mM of adenosine and/or uridine.

A variety of antioxidants may be used or present in the composition. Suitable antioxidants include manganese, vitamin E and manganous phosphate, Mn-peptides, Mn-amino acids (e.g., Leucine), Mn-TRIS, Mn-melanin, Mn-caffeine, Mn-ribose, Mn-trehalose, Mn-dipicolinic acid, Mn-phosphate and Mn-bacarobonate. In one embodiment of the invention, the antioxidant is manganese. In another embodiment, the antioxidant is $MnCl_2$. In yet another embodiment, the antioxidant is vitamin E and/or aspirin. The amount of antioxidant in the composition varies in its use. Those of skill in the art will be able to determine the suitable amount. In one embodiment, the composition contains about 0.01 mM to about 15 mM of the antioxidant. In another embodiment, the composition contains about 0.01 mM to about 12.5 mM.

In one embodiment of the invention, one antioxidant is manganous phosphate which may be provided as a mixture. In one embodiment the mixture is produced by mixing a solution of manganese and a solution of phosphate. The amount of antioxidant in the composition varies on its use. Those of skill in the art will be able to determine the suitable amount. In one embodiment, the compositions comprise from about 0.01 mM to about 15 mM of the manganous (Mn(II)) ions. In a more specific embodiment, the compositions comprise from about 0.01 mM to about 15 mM of the manganous (Mn(II)) ions in a phosphate buffer. In a still more specific embodiment, the compositions comprise phosphate buffer at a concentration of from about 1 mM to about 25 mM. In one specific embodiment, the mixture is a 1 mM solution of Mn(II) and a solution of 25 mM phosphate buffer (ph 7.4).

The compositions contain one or more amino acids that exhibit cytoprotective properties. In one embodiment of the invention, the composition further contains at least one or more amino acid selected from the group consisting of aspartate, glutamate, serine, histidine, glycine, threonine, arginine, tyrosine, methionine, phenylalanine, isoleucine, lysine, ornithine, leucine, valine and alanine. In another embodiment, the amino acid is leucine. In an alternate embodiment, the amino acid is glycine. In another embodiment, the compositions include at least leucine and alanine. In another embodiment, the composition does not contain proline. In still another embodiment, the composition contains 10% or less proline as measured against the presence of other amino acids. For example, an equal mixture of 12 distinct amino acids would contain 1 proline residue or less in this embodiment.

As an alternative, or in addition to the presence of individual amino acids, the compositions and the methods using these compositions may comprise at least one small peptide such as, but not limited to, a decpeptide. As used herein, "small peptide" means a small, linear chain of amino acids of no more than about 25 residues in length. In one embodiment, the small peptides used in the compositions or methods of the present invention are about 25, 24, 23, 22, 21, 20, 19, 18, 17, 16, 15, 14, 13, 12, 11, 10, 9, 8, 7, 6, 5, 4, 3 or 2 amino acids in length. The actual sequence of the peptide is not critical to the compositions and methods of the present invention, thus any random peptide chain will suffice. For example, in one embodiment, the compositions and methods using these compositions may comprise at least one small peptide, wherein the small peptide comprises an amino acid sequence that is at least about 80% identical to the amino acid sequence of SEQ ID NO:1: Asp-Glu-His-Gly-Thr-Ala-Val-Met-Leu-Lys (SEQ ID NO:1). In one embodiment, the small peptide contains no proline residues. In another embodiment, the peptide contains less that 10% of proline residues as compared to other amino acids. For example, in this specific embodiment, a 12-mer would contain one proline residue or less.

In still further embodiments, each of the small peptides independently comprise an amino acid sequence at least 60%, 70%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:1. Small peptides that are less than 100% identical to the amino acid sequence of SEQ ID NO:1 are considered variants thereof.

The amount of small peptide will vary. Those of skill in the art will be able to determine the suitable amount depending on a variety of factor such as the subject, the duration of the radiation exposure, the amount of the radiation exposure, etc. In some embodiments of the invention, the amount of small peptide ranges from about 0.01 mM to about 15 mM, from about 0.1 mM to about 1 mM, from about 1 mM to about 10 mM, from about 1 mM about 15 mM. In one embodiment, the concentration of one or more small peptide comprises about 1 mM to about 15 mM of the peptide of SEQ ID NO:1 or variants thereof. In other embodiments, the concentration of one or more small peptides comprises about 15 mM or less, about 14 mM or less, about 13 mM or less, about 12 mM or less, about 11 mM or less, about 10 mM or less, about 9 mM or less, about 8 mM or less, about 7 mM or less, about 6 mM or less, about 5 mM or less, about 4 mM or less, about 3 mM or less, about 2 mM or less, about 1 mM or less or about 0.5 mM or less of the peptide of SEQ ID NO:1. Of course, the concentration of one or more small peptides can be in between any of the listed concentrations, for example between about 15 mM and about 14 mM, between about 14 mM and about 13 mM, between about 13 mM and about 12 mM, between about 12 mM and about 11 mM, between about 11 mM and about 10 mM, between about 10 mM and about 9 mM, between about 9 mM and about 8 mM, between about 8 mM and about 7 mM, between about 7 mM and about 6 mM, between about 6 mM and about 5 mM, between about 5 mM and about 4 mM, between about 5 mM and about 3 mM, between about 3 mM and about 2 mM, between about 2 mM and about 1 mM, between about 1 mM and about 0.5 mM, etc of the peptide of SEQ ID NO:1 or variants thereof.

A polypeptide having an amino acid sequence at least, for example, about 95% "identical" to a reference amino acid sequence, e.g., SEQ ID NO:1, is understood to mean that the amino acid sequence of the polypeptide is identical to the reference sequence except that the amino acid sequence may include up to about five modifications per each 100 amino acids of the reference amino acid sequence. In other words, to obtain a peptide having an amino acid sequence at least about 90% identical to a reference amino acid sequence, up to about 10% of the amino acid residues of the reference sequence may be deleted or substituted with another amino acid or a number of amino acids up to about 10% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there are several methods to measure identity between two polynucleotide or polypeptide sequences, the term "identity" is well known to skilled artisans (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCG program package (Devereux, J., et al., Nucleic Acids Research 12(i):387 (1984)), BLASTP, ExPASy, BLASTN, FASTA (Atschul, S. F., et al., J Molec Biol 215:403 (1990)) and FASTDB. Examples of methods to determine identity and similarity are discussed in Michaels, G. and Garian, R., Current Protocols in Protein Science, Vol 1, John Wiley & Sons, Inc. (2000), which is incorporated by reference.

In one embodiment of the present invention, the algorithm used to determine identity between two or more polypeptides is BLASTP. In another embodiment of the present invention, the algorithm used to determine identity between two or more polypeptides is FASTDB, which is based upon the algorithm of Brutlag et al. (Comp. App. Biosci. 6:237-245 (1990), incorporated by reference). In a FASTDB sequence alignment, the query and reference sequences are amino sequences. The result of sequence alignment is in percent identity. Parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the reference sequence is shorter or longer than the query sequence because of N-terminus or C-terminus additions or deletions, but not because of internal additions or deletions, a manual correction can be made, because the FASTDB program does not account for N-terminus and C-terminus truncations or additions of the reference sequence when calculating percent identity. For query sequences truncated at the N- or C-termini, relative to the reference sequence, the percent identity is corrected by calculating the number of residues of the query sequence that are N- and C-terminus to the reference sequence that are not matched/aligned, as a percent of the total bases of the query sequence. The results of the FASTDB sequence alignment determine matching/alignment. The alignment percentage is then subtracted from the percent identity, calculated by the above FASTDB program using the specified parameters, to arrive at a final percent identity score. This corrected score may be used for the purposes of determining how alignments "correspond" to each other, as well as percentage identity. Residues of the reference sequence that extend past the N- or C-termini of the query sequence may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue query sequence is aligned with a 100 residue reference sequence to determine percent identity. The deletion occurs at the N-terminus of the query sequence and therefore, the FASTDB alignment does not show a match/alignment of the first 10 residues at the N-terminus. The 10 unpaired residues represent 10% of the reference sequence (number of residues at the N- and C-termini not matched/total number of residues in the reference sequence) so 10% is subtracted from the percent identity score calculated by the FASTDB program. If the remaining 90 residues were perfectly matched (100% alignment) the final percent identity would be 90% (100% alignment −10% unmatched overhang). In another example, a 90 residue query sequence is compared with a 100 reference sequence, except that the deletions are internal deletions. In this case the percent identity calculated by FASTDB is not manually corrected, since there are no residues at the N- or C-termini of the subject sequence that are not matched/aligned with the query. In still another example, a 110 amino acid query sequence is aligned with a 100 residue reference sequence to determine percent identity. The addition in the query occurs at the N-terminus of the query sequence and therefore, the FASTDB alignment may not show a match/alignment of the first 10 residues at the N-terminus. If the remaining 100 amino acid residues of the query sequence have 95% identity to the entire length of the reference sequence, the N-terminal addition of the query would be ignored and the percent identity of the query to the reference sequence would be 95%.

In one embodiment, the compositions comprise adenosine, uridine, leucine, adenine, and manganese. In another embodiment, the composition comprises about 1 to about 15 mM adenosine and about 1 to about 12.5 mM $MnCl_2$. In another embodiment, the composition comprises a *D. radiodurans* extract containing one or more nucleosides and one or more antioxidants.

Any protein function may be preserved by use of the methods of this invention. In a preferred embodiment of the invention, the protein is an enzyme. The methods of the instant disclosure are particularly useful in preventing protein oxidation associated with ultraviolet radiation and aging. Furthermore, the methods also preserve protein functionality during desiccation and thus help increase the shelf life of desiccated blood products and enzyme-based drugs, which are stored dry.

The methods of the invention optimally preserve protein function (such as e.g., enzymatic activity) during exposure to radiation. One embodiment of the invention is a method of preservation comprising contacting a protein (such as e.g., an enzyme) with a composition comprising one or more nucleosides and one or more antioxidants.

Another embodiment of the invention is a method of increasing the durability and longevity of microbial and enzyme-driven fuel cells comprising contacting the components of the fuel cell with a composition comprising one or more nucleosides and one or more antioxidants.

This method may be suitable to preserve the function of many proteins including but not limited to proteins with Fe—S complexes (such as metabolic enzymes) and enzymatic repair functions that are dependent on redox-active (4Fe-4S) clusters. Exemplary proteins include protein groups associated with the production of reactive oxygen species (ROS), transport protein precursors which might reduce biosynthetic demands and suppress the production of ROS, proteins that defend against ROS, proteins that participate in repair of damaged molecules (non-DNA) and redox regulation as well as Mn and Fe-dependent systems. Other exemplary proteins are listed in Ghosal et al. (2005), FEMS Microbiology Reviews 29: 361-375, the disclosure of which is herein incorporated in its entirety.

The invention also provides methods of producing vaccines directed against microorganisms, with the methods comprising culturing, harvesting, and/or suspending the microorganism in the presence of a radiation-protective composition of the present invention and irradiating the bacteria with a dose of radiation sufficient to render the microorganism replication-deficient. In one embodiment, the radiation protective composition is synthetic; in another embodiment, the radiation protective composition is DR ultrafiltrate extract.

Methods of vaccine preparation are well known in the art. The methods provided herein can be applied to these well-known vaccine preparation methods, or they can be used separately and apart from traditional vaccine preparation methods. For example, one embodiment of the present invention provides for methods of vaccine preparation without genetically engineering the microorganism against which the vaccine is being prepared. The methods disclosed herein allow for normal, wild-type microorganisms to be cultured, harvested, and/or suspended in the presence of the radiation-protective compositions, such that the three-dimensional structure of the proteins within and the cell surface markers on the microorganisms is preserved during an extreme dose of radiation. The dose of radiation is designed to obliterate the genome of the microorganism such that the microorganism is incapable of replication. After dosing with radiation, the replication-deficient cells can be collected and vaccine preparation can be carried out using normal vaccine preparatory techniques. The protective compositions of the present invention preserve at least a fraction of the immunogenic proteins of the microorganism, such that administration of a vaccine comprising the irradiated microorganism to an animal will produce an immunogenic response. Thus, the present methods of vaccine preparation can be practiced using routine cell culture techniques. The microoganisms against which a vaccine can be prepared using the methods of the present invention include bacteria and viruses. Standard cell culture techniques for bacteria and viruses are well known in the art.

Of course, the vaccine preparation methods of the present invention are not limited to a particular type of radiation, provided the type and dose used is capable of rendering the microorganism replication defective. Examples of radiation include but are not limited to, UV light, alpha radiation, beta radiation, gamma radiation, X-ray radiation and neutron radiation. In one embodiment, the dose of radiation is at least about 20 kGy. The dose of radiation may be over 25,000 Gy (25 kGy) for bacterial mixtures and the dose of radiation may be over 40,000 Gy (40 kGy) for viral mixtures.

The invention also provides methods of rendering bacteria in culture resistant to ionizing radiation (IR), with these methods comprising culturing the bacteria in the presence of a radiation-protective composition of the present invention. The radiation-protective compositions used in IR-resistant methods of the present invention comprise at least one nucleoside, phosphate, at least one antioxidant and any non-metabolizable hydroxyl-radical scavengers, such as but not limited to, dimethyl sulfoxide (DMSO).

The invention also provides for methods of treating or preventing the effects of radiation exposure. The methods comprise treating or preventing the effects of radiation exposure with a therapeutic agent comprising one or more nucleosides and one or more antioxidants.

In one embodiment of the invention, the radiation exposure is due to UV exposure. In another embodiment of the invention, the radiation exposure is due to ionizing radiation. In another embodiment of the invention, the radiation exposure is chronic.

As used herein, the term "therapeutic agent" shall encompass compositions comprising one or more nucleosides and one or more antioxidants as well as formulations containing other pharmaceutically acceptable components such as e.g. pharmaceutically acceptable carriers.

As used herein, the term "radiation exposure" shall mean exposure to any radiation in a dose and for a period sufficient to cause damage. Radiation exposure includes but it is not limited to exposure to UV light, alpha radiation, beta radiation, gamma radiation, X-ray radiation and neutron radiation.

In one embodiment, the invention provides for methods of treating or preventing the side effects of radiotherapy. As used herein, the term "radiotherapy" shall refer to the use of certain types of energy (such as e.g., ionizing radiation) to kill cancer cells and shrink tumors. The term "radiotherapy" includes all types of radiotherapy including but not limited to external radiation therapy (such as e.g., intraoperative radiotherapy and prophylactic cranial irradiation (PC)), internal radiation therapy (such as e.g., interstitial radiation therapy, intracavitary or intraluminal radiation therapy), systemic radiation therapy, stereotactic (or stereotaxic) radiosurgery, three-dimensional (3-D) conformal radiation therapy, intensity-modulated radiation therapy (IMRT). Furthermore, the term "radiotherapy" also encompasses radiotherapy using a variety of sources of radiation including but not limited to X-rays, gamma rays, particle beams, proton beam therapy, and high-energy photon radiation. Radiotherapy is used to treat a variety of cancers including solid tumors (such as e.g., cancers of the brain, breast, cervix, larynx, lung, pancreas, prostate, skin, spine, stomach, uterus, or soft tissue sarcomas). Radiotherapy is also used to treat leukemia and lymphoma (i.e., cancers of the blood-forming cells and lymphatic system, respectively) as well as cancers of the skin, cervix, and thyroids.

As used herein, the term "side effects of radiotherapy" shall be refer to any side effect experienced by a subject undergoing radiotherapy. Such side effects include but are not limited to tiredness and skin reactions, anemia, increased risk of bruising or bleeding, decreased fertility, dry mouth, loss of appetite and weight, hair loss etc.

A "subject in need of treatment" is an animal with a bacterial infection that is potentially life-threatening or that impairs health or shortens the lifespan of the animal. The animal can be a fish, bird, or mammal. Exemplary mammals include humans, domesticated animals (e.g., cows, horses, sheep, pigs, dogs, and cats), and exhibition animals, e.g., in a zoo. In a preferred embodiment, the subject is human.

The terms "treating", "treatment," and "therapy" as used herein refer to curative therapy, prophylactic therapy, and preventative therapy.

As used herein, unless stated otherwise, the term composition is meant to encompass, and not limited to, pharmaceutical compositions and nutraceutical compositions containing one or more nucleosides and one or more antioxidants. The composition may also contain one or more "excipients" that are "inactive ingredients" or "compounds" devoid of pharmacological activity or other direct effect in the diagnosis, cure, mitigation, treatment, or prevention of disease or to affect the structure or any function of the human body.

A "pharmaceutically acceptable" component is one that is suitable for use with humans, animals, and/or plants without undue adverse side effects (such as e.g., toxicity, irritation, and allergic response) commensurate with a reasonable benefit/risk ratio.

The therapeutic agent may contain any nucleoside. Suitable nucleosides include but are not limited to adenosine, uridine, β-pseudouridine, inosine, and mixtures thereof. In one embodiment, the nucleoside is adenosine and/or uridine. In one embodiment, the therapeutic agent contains adenosine. In other embodiment of the invention, the therapeutic agent contains uridine.

The therapeutic agent may contain a variety of suitable antioxidants, which have been disclosed herein. For example, suitable antioxidants include but are not limited to manganese, vitamin E, and manganous-phosphate, Mn-peptides, Mn-amino acids (e.g., Leucine), Mn-TRIS, Mn-melanin, Mn-caffeine, Mn-ribose, Mn-trehalose, Mn-dipicolinic acid, Mn-phosphate and Mn-bacarobonate. In one embodiment of the invention, the antioxidant of the therapeutic agent is manganese. In another embodiment, the antioxidant is $MnCl_2$. In yet another embodiment, the antioxidant is one or more peptides.

In one embodiment of the invention, a critical antioxidant is manganous phosphate, which may be provided at near-millimolar concentrations. In another embodiment, the antioxidant is $MnCl_2$, with phosphate added separately. The phosphate may or may not be orthophosphate. The amount of antioxidant in the composition varies on its use. Those of skill in the art will be able to determine the suitable amount. In one embodiment, the composition contains about 0.01 mM to about 15 mM of the manganous (Mn(II)) ions and 1 mM to about 25 mM phosphate buffer.

The amount of nucleoside and antioxidant in the therapeutic agent varies. Those of skill in the art will be able to determine the suitable amount depending on a variety of factor such as the subject, the duration of the radiation exposure, the amount of the radiation exposure etc. In some embodiments of the invention, the amount of nucleoside ranges from about 0.01 mM to about 15 mM, from about 0.1 mM to about 1 mM, from about 1 mM to about 10 mM, from about 1 mM about 15 mM. In one embodiment, the concentration of one or more nucleosides comprises about 1 mM to about 15 mM of adenosine and/or uridine. In another embodiment, the amount of antioxidant ranges from about 0.01 mM to about 15 mM. In another embodiment, the therapeutic agent contains about 0.01 mM to about 12.5 mM.

The therapeutic agent may further contain one or more amino acids that exhibit cytoprotective properties. In one embodiment of the invention, therapeutic agent further contains at least one or more amino acid selected from the group consisting of leucine, valine, and alanine. In another embodiment, the amino acid is leucine. In another embodiment, the amino acid is glycine.

In one embodiment, the therapeutic agent comprises adenosine, uridine, leucine, adenine, and manganese. In an alternate embodiment, the therapeutic agent comprises about 1 mM to about 15 mM adenosine and about 1 mM to about 12.5 mM $MnCl_2$. In another embodiment, the therapeutic agent comprises a D. radiodurans extract containing one or more nucleosides and one or more antioxidants.

In yet another embodiment of the invention, the therapeutic agent is a composition suitable for human use comprising one or more nucleoside (such as e.g., adenosine, uridine, β-pseudouridine, inosine, and mixtures thereof), one or more antioxidant (such as e.g., manganese, peptides, and vitamin E) and optionally one or more amino acid selected from the group consisting of leucine, valine, and alanine. In one embodiment, the composition suitable for human use comprises adenosine and manganese.

In an alternate embodiment of the invention, the therapeutic agent is a D. radiodurans extract containing one or more nucleosides and one or more antioxidants.

The methods for treating or preventing the effects of radiation exposure comprise administration of a therapeutic agent comprising one or more nucleosides and one or more antioxidants to a subject in need thereof.

One embodiment is a method of preventing a side effect of radiotherapy, comprising administration of a D. radiodurans extract comprising one or more nucleosides and one or more antioxidants to a subject in need thereof.

Another embodiment of the invention is a method of preventing a side effect of radiotherapy comprising administration of a composition comprising one or more nucleosides, an antioxidant and optionally an amino acid selected from the group consisting of alanine, valine and leucine to a subject in need thereof. Preferably the one or more nucleoside is adenosine and/or uridine, which may be present in amounts from about 1 mM to about 15 mM of adenosine and/or uridine. The one or more nucleosides may also selected from the group consisting of adenosine, uridine, β-pseudouridine, inosine, and mixtures thereof. The antioxidant may be manganese (e.g. of about 1 mM to about 12.5 mM). In one embodiment, the antioxidant is $MnCl_2$. In another embodiment, the antioxidant is one or more peptides. In another embodiment, the composition comprises adenosine, uridine, leucine, adenine, and manganese.

The methods of the instant application are particularly advantageous. Compared to well-established radioprotectors (such e.g. amifostine), compositions comprising one or more nucleosides and one or more antioxidants (e.g., adenosine, uridine, peptides and Mn) are relatively non-toxic.

The methods of the invention are particularly suitable for pre- and post-exposure treatments of military personnel and civilians accidentally or deliberately exposed to ionizing radiation.

The methods may also used prophylactically for individuals exposed to significant chronic levels of radiation such as in nuclear power plants, during long-duration space flight, or on the international space station.

A "safe and effective amount" refers to a quantity of a component that is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a component effective to yield a desired therapeutic response, e.g., an amount effective to slow the rate of bacterial cell division, or to cause cessation of bacterial cell division, or to cause death or decrease rate of population growth of the bacteria. The specific safe and effective amount or therapeutically effective amount will vary with such factors as the particular condition being treated, the physical condition of the subject, the type of subject being treated, the duration of the treatment, the nature of concurrent therapy (if any), and the specific formulations employed and the structure of the compounds or its derivatives.

Means of application include, but are not limited to direct, indirect, carrier and special means or any combination of means. Direct application of the phage may be by nasal sprays, nasal drops, nasal ointments, nasal washes, nasal injections, nasal packings, bronchial sprays and inhalers, or indirectly through use of throat lozenges, or through use of mouthwashes or gargles, or through the use of ointments applied to the nasal nares, the bridge of the nose, or the face or any combination of these and similar methods of application. The forms in which the phage may be administered include but are not limited to lozenges, troches, candies, injectants, chewing gums, tablets, powders, sprays, liquids, ointments, and aerosols.

The therapeutic agent may also be placed in a nasal spray, wherein the nasal spray is the carrier. The nasal spray can be a long acting or timed release spray, and can be manufactured by means well known in the art. An inhalant may also be used, so that the therapeutic agent may reach further down into the bronchial tract, including into the lungs.

The therapeutic agent may be added to these substances in a liquid form or in a lyophilized state, whereupon it will be solubilized when it meets body fluids such as saliva. The enzyme may also be in a micelle or liposome.

While these methods may be used in any mammalian species such as farm animals including, but not limited to, horses, sheep, pigs, chicken, and cows, the preferred use of compositions is for a human.

The effective dosage rates or amounts of the compositions will depend in part on whether the composition will be used therapeutically or prophylactically, the duration of exposure of the recipient to radiation, the type of radiation, the size, and weight of the individual, etc. The duration for use of the composition also depends on whether the use is for prophylactic purposes, wherein the use may be hourly, daily or weekly, for a short time period, or whether the use will be for therapeutic purposes wherein a more intensive regimen of the use of the composition may be needed, such that usage may last for hours, days or weeks, and/or on a daily basis, or at timed intervals during the day. Any dosage form employed should provide for a minimum number of units for a minimum amount of time. The concentration of the active units of phage believed to provide for an effective amount or dosage of phage may be in the range of about 100 units/ml to about 100,000 units/ml of fluid in the wet or damp environment of the nasal and oral passages, and possibly in the range of about 100 units/ml to about 10,000 units/ml. More specifically, time exposure to the radiation may influence the desired concentration of active radioprotective composition units per ml. It should be noted that carriers that are classified as "long" or "slow" release carriers (such as, for example, certain nasal sprays or lozenges) could possess or provide a lower concentration of the composition per ml, but over a longer period of time, whereas a "short" or "fast" release carrier (such as, for example, a gargle) could possess or provide a high concentration of composition per ml, but over a shorter period of time. It will furthermore be appreciated that a therapeutically effective amount of a particular composition can be determined by those of ordinary skill in the art with due consideration of the factors pertinent to the subject.

Selection of the preferred effective dose can be determined (e.g., via clinical trials) by a skilled artisan based upon the consideration of several factors which will be known to one of ordinary skill in the art. Such factors include the disease to be treated or prevented, the symptoms involved, the patient's body mass, the patient's immune status and other factors known by the skilled artisan to reflect the accuracy of administered pharmaceutical compositions.

The precise dose to be employed in the formulation will also depend on the route of administration and should be decided according to the judgment of the practitioner and each patient's circumstances. Effective doses may be extrapolated from dose-response curves derived from in vitro or animal model test systems.

For the prophylactic and therapeutic treatment and/or prevention of the effects of radiation exposure, the compositions comprising nucleosides and antioxidants may also be applied by direct, indirect, carriers and special means or any combination of means. Direct application of the phage may be by nasal sprays, nasal drops, nasal ointments, nasal washes, nasal injections, nasal packings, bronchial sprays and inhalers, or indirectly through use of throat lozenges, or through use of mouthwashes or gargles, or through the use of ointments applied to the nasal nares, the bridge of the nose, or the face or any combination of these and similar methods of application. The forms in which the phage may be administered include but are not limited to lozenges, troches, candies, injectants, chewing gums, tablets, powders, sprays, liquids, ointments, and aerosols. For the therapeutic treatment of anthrax, the bronchial sprays and aerosols are most beneficial, as these carriers, or means of distributing the composition, allow the phage to reach the bronchial tubes and the lungs.

The compositions of the present invention can be administered via parenteral, subcutaneous, intravenous, intramuscular, intraperitoneal, transdermal, or buccal routes. For example, an agent may be administered locally to a site of injury via microinfusion. Alternatively, or concurrently, administration may be by the oral route. The dosage administered will be dependent upon the age, health, and weight of the recipient, kind of concurrent treatment, if any, frequency of treatment, and the nature of the effect desired.

In one embodiment of the invention, the method comprises administration of the therapeutic agent in a pharmaceutically acceptable carrier. Suitable carriers and their formulations are described in Remington's Pharmaceutical Sciences, 2005, Mack Publishing Co. Typically, an appropriate amount of a pharmaceutically acceptable salt is used in the formulation to render the formulation isotonic. Examples of the pharmaceutically acceptable carrier include liquids such as saline, Ringer's solution, and dextrose solution. The pH of the solution is preferably from about 5 to about 8, and more preferably from about 7 to about 7.5. The formulation may also comprise a lyophilized powder. Further carriers include sustained release preparations such as semi-permeable matrices of solid hydrophobic polymers, which matrices are in the form of shaped articles, e.g., films, liposomes or microparticles. It will be apparent to those persons skilled in the art that certain carriers may be more preferable depending upon, for instance, the route of administration and concentration of proinflammatory cytokine inhibitor being administered.

The methods optimally provide therapeutics against numerous redox-related forms of cell injury mediated by protein damage, and facilitate wound healing.

One embodiment of the invention is a method of preparing $D.$ $radiodurans$ cell-free ultrafiltrate extracts that exhibit radio-protective properties. In one embodiment, the methods comprise harvesting a $D.$ $radiodurans$ by e.g., centrifugation, lysing the $D.$ $radiodurans$ culture to create a lysate, washing the $D.$ $radiodurans$ lysate followed by centrifuging the lysate for a time and under conditions sufficient to create a supernatant. After centrifugation, the supernatant is passed through a microfilter, preferably a 3 kiloDalton microfilter, and boiled for a period for a suitable amount of time. In one embodiment, the supernatant is boiled for about 15 to about 45 minutes after filtration. The resulting $D.$ $radiodurans$ extract contains one or more nucleosides and one or more antioxidants, is soluble in butanol, resistant to boiling, and cell-free.

In one embodiment, the extract contains adenosine and manganese. In another embodiment, the extract contains adenosine and/or uridine manganese. The cell extracts may also further contain leucine, alanine, and/or valine. In one embodiment, the $D.$ $radiodurans$ extract contains at least adenosine, uridine, leucine, adenine, and manganese.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

EXAMPLES

Example 1—Preparation of Protein-Free Extract from $D.$ $radiodurans$ $D.$ $radiodurans$ (ATTC BAA-816) was grown to OD600 0.9 in TGY, harvested by centrifugation, and lysed by French pressure treatment. The cells were washed and then lysed in double-distilled, de-ionized sterile water ($dH_2O$). Prior to lysis, cell density was adjusted with $dH_2O$ to yield lysates representing approximately 50% intracellular concentration. Crude cell extracts were centrifuged for 20 hours at 175,000×g. The supernatant was passed through a <3 kiloDalton Microcon centrifugal filter (Millipore, USA) and boiled for 30 min. The Coomassie (Bradford) protein assay was used to confirm the virtual absence of proteins in the ultra-purified extracts, which were aliquoted and stored at −80° C.

Example 2—Analysis of Protein-Free Extract from $D.$ $radiodurans$

The ultrafiltered cell extracts were prepared from $D.$ $radiodurans$ (ATCC BAA-816), $P.$ $putida$ (ATCC 47054), $E.$ $coli$ (MG1655), and $T.$ $thermophilus$ (ATCC BAA-163). M. E. Maguire provided wild-type $E.$ $coli$ (MM1925, strain K12) and its isogenic mntHmutant (MM2115). $D.$ $radiodurans$ recA- (rec30) and $E.$ $coli$ recA- (DH10B) are known in the art. The Jurkat T cell line was ATCC TIB-152. The DR-, PP-, EC- and TT-ultrafiltrates were prepared from bacteria grown as batch cultures in TGY medium to the same optical density at 600 nm (0.9; log-phase). For large-scale production of DR-ultrafiltrate used in the $E.$ $coli$ and Jurkat T cell radioprotection studies, high cell-density growth of $D.$

*radiodurans* was in a 20 L fermentor. The cells were broken open by passage through a French Press. In the following order, bacterial lysates were centrifuged at 12,000×g (1 h, 4° C.); the supernatants were standardised for concentration on a protein-basis and ultracentrifuged at 190,000×g (48 h, 4° C.); and the ultracentrifuged supernatants were subjected to filtration through 3 kDa filters. The ultrafiltrates were boiled for 40 min, concentrated 5 times, and stored at −80° C. The chemical composition of the DR-, PP-, EC- and TT-ultrafiltrates were determined as follows: Mn and Fe on a Perkin Elmer model 4100ZL atomic absorption spectrometer; inorganic phosphate by the malachite green assay; bases, nucleosides and nucleotides by HPLC; protease activity with azocasein as substrate; and amino acids by pre-column derivatisation as implemented by Agilent Technologies.

Example 3—Radioprotective Effects in *E. Coli*

Individually and in combination, the radioprotective properties of $Mn^{2+}$, phosphate, uridine and DMSO were determined using *E. coli* grown in TGY medium; TGY is a peptide-rich medium based on yeast extract, and contains approximately 200 nM Mn. At 3 kGy, supplementation of TGY with 1 μM $Mn^{2+}$ did not increase the resistance of *E. coli*; supplementation of TGY with 13 mM phosphate increased the resistance of *E. coli* by 800 times; and supplementation of TGY with either 3 mM uridine or 384 mM (3%) DMSO increased the resistance of *E. coli* by 50 times. When these agents were combined at concentrations applied individually, the survival of *E. coli* exposed to 3 kGy was increased by 10,000 times.

Example 4—The Reconstituted $Mn^{2+}$ Peptide Complex

The extremely radioprotective $Mn^{2+}$-decapeptide-phosphate complex is based on a consensus amino acid sequence (H-Asp-Glu-His-Gly-Thr-Ala-Val-Met-Leu-Lys-OH) (SEQ ID NO: 1) of hundreds of peptides purified from *D. radiodurans*. The composition of the mixture which spontaneously forms the $Mn^{2+}$ complex comprises 3 mM (H-Asp-Glu-His-Gly-Thr-Ala-Val-Met-Leu-Lys-OH) (SEQ ID NO: 1), 1 mM $MnCl_2$, 25 mM orthophosphate (Pi) buffer (pH 7.4). When reconstituted in vitro, the $Mn^{2+}$ complexes preserved the activity of enzymes exposed to 50,000 Gy. Studies with the decapeptides have demonstrated that it is the amino acid composition of the decapeptide, not the specific sequence of amino acids, which is critical to its radioprotective properties when combined with $Mn^{2+}$ and orthophosphate buffer. The peptides need not be limited to 10 amino acids, but instead be comprised of the specific amino acids present in the above decapeptide.

Figure 5:
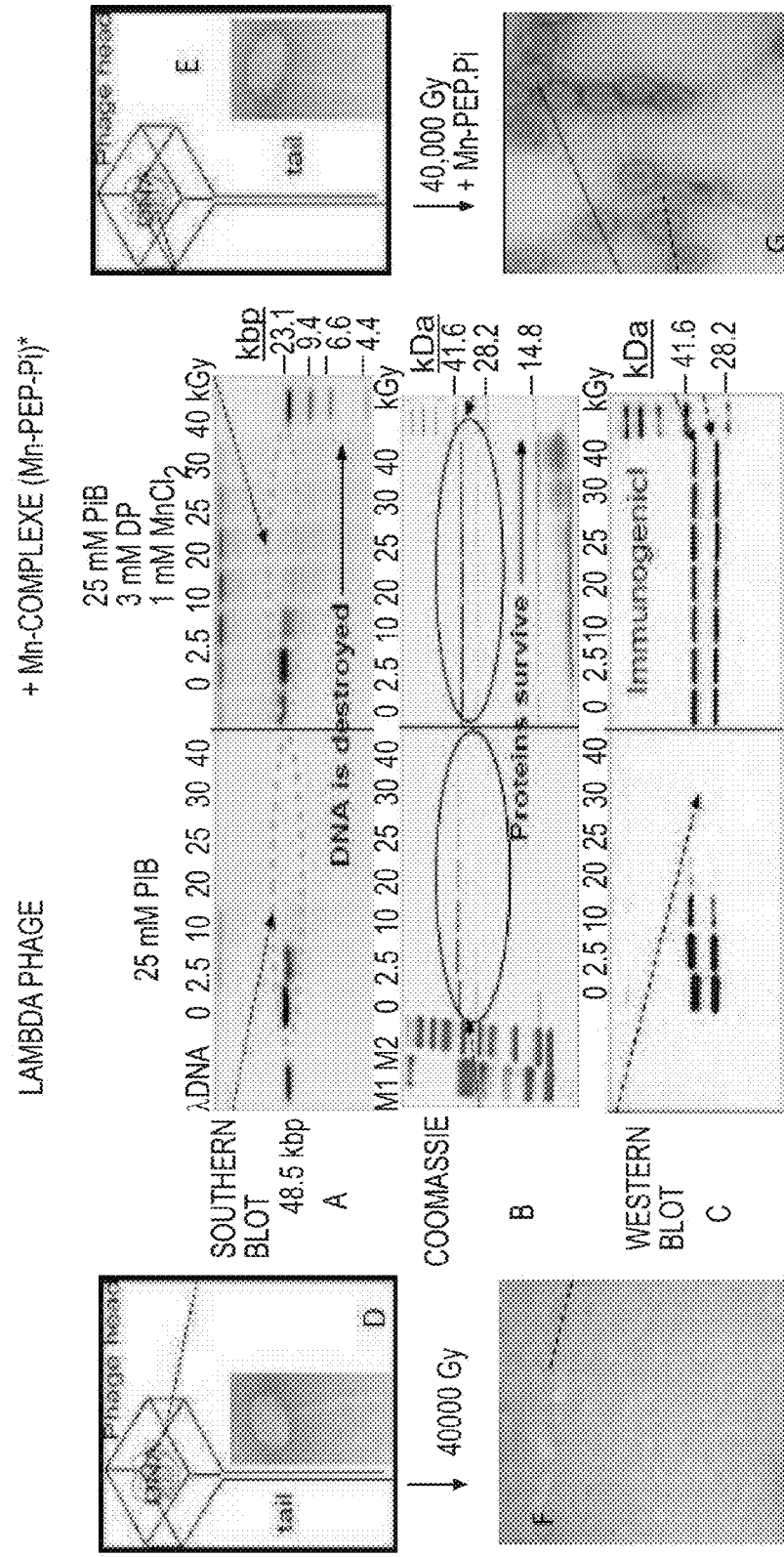
FIG. 5 depicts the approach for irradiated vaccine preparation with the manganese complex. (A) DNA was prepared from irradiated bacteriophage λ treated (right) or not (left) with the $Mn^{2+}$ complex (Mn-pep-Pi): 3 mM (H-Asp-Glu-His-Gly-Thr-Ala-Val-Met-Leu-Lys-OH) (SEQ ID NO: 1), 1 mM $MnCl_2$, 25 mM orthophosphate (Pi) buffer (pH 7.4). At the indicated gamma-ray doses (0-40 kGy), DNA (48.5 kbp genome) was purified from bacteriophage λ, subjected to conventional agarose gel electrophoresis, and then to Southern blotting with a radiolabelled λ DNA probe. Conclusion: The $Mn^{2+}$ complex does not significantly protect DNA packaged in viruses. (B) The same bacteriophage λ preparations as examined in panel A were tested for protein integrity by separating the virus proteins using polyacrylamide gel electrophoresis. Conclusion: Proteins in viruses which were irradiated in the absence of the $Mn^{2+}$ complex (left) were progressively destroyed. In contrast, the proteins in the virus samples which contained the $Mn^{2+}$ complex (right) were not affected by doses as high as 40 kGy. (C) At 40,000 Gy, a dose which obliterated the virus DNA (panel A) and rendered the virus completely non-infective (not shown), the virus proteins remained fully immunogenic. This was tested by Western analysis, whereby λ proteins were challenged with antibodies raised in rabbits against non-irradiated λ phage. Note, an identical positive result for immunogenicity was obtained for equivalent Westerns probed with antibodies raised against λ phage exposed to 40,000 Gy in the presence of the $Mn^{2+}$ complex. In contrast, λ phage exposed to 40,000 Gy in the absence of the $Mn^{2+}$ complex did not yield antibodies in rabbits which had significant specificity for native bacteriophage λ. (D) and (E): Transmission electron micrograph (TEM) of λ phage pre-irradiation—treated (E) or untreated (D) with $Mn^{2+}$ complex. (F) and (G): TEM of λ phage post-irradiation (40 kGy) treated (G) or not (F) with the $Mn^{2+}$ complex. In the presence of the $Mn^{2+}$ complex, the λ phage virus particles exposed to 40 kGy were undamaged.

Example 5—Application of Reconstituted *D. radiodurans* $Mn^{2+}$ Complexes for the Production of Irradiated Vaccines Irradiating bacteria using the methods described herein was tested and validated at 40,000 Gy using the model bacteriophage Lambda virus (FIG. 5). DNA was prepared from irradiated bacteriophage λ treated or not with the $Mn^{2+}$ complex (Mn-pep-Pi): 3 mM (H-Asp-Glu-His-Gly-Thr-Ala-Val-Met-Leu-Lys-OH) (SEQ ID NO: 1), 1 mM $MnCl_2$, 25 mM orthophosphate (Pi) buffer (pH 7.4). At the indicated gamma-ray doses (0-40 kGy), DNA (48.5 kbp genome) was purified from bacteriophage λ, subjected to conventional agarose gel electrophoresis, and then to Southern blotting with a radiolabelled λ DNA probe. As shown in FIG. 5A, the $Mn^{2+}$ complex does not significantly protect DNA packaged in viruses.

The same bacteriophage λ preparations as examined in FIG. 5A were tested for protein integrity by separating the virus proteins using polyacrylamide gel electrophoresis. As shown in FIG. 5B, proteins in viruses which were irradiated in the absence of the $Mn^{2+}$ complex were progressively destroyed. In contrast, the proteins in the virus samples which contained the $Mn^{2+}$ complex were not affected by doses as high as 40 kGy.

At 40,000 Gy, a dose which obliterated the virus DNA (see FIG. 5A) and rendered the virus completely non-infective, the virus proteins remained fully immunogenic. This was tested by Western analysis, whereby λ proteins were challenged with antibodies raised in rabbits against non-irradiated λ phage. An identical positive result for immunogenicity was obtained for equivalent Westerns probed with antibodies raised against λ phage exposed to 40,000 Gy in the presence of the $Mn^{2+}$ complex. In contrast, λ phage exposed to 40,000 Gy in the absence of the $Mn^{2+}$ complex did not yield antibodies in rabbits which had significant specificity for native bacteriophage λ.

Figure 6:
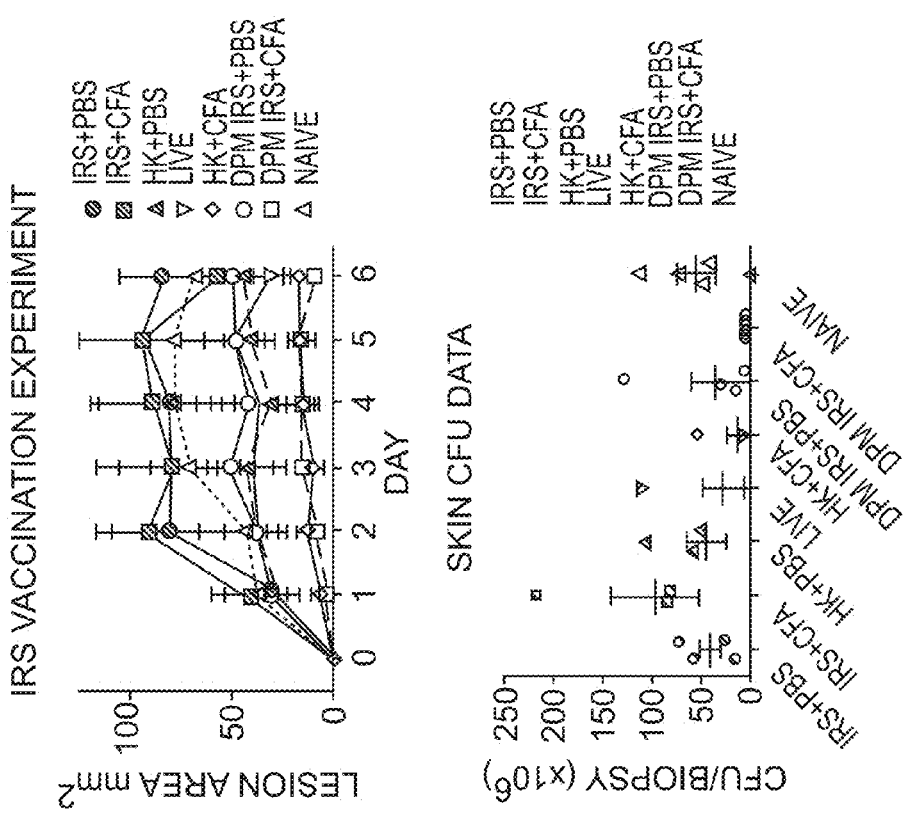
FIG. 6 depicts tabular and graphical data from mice tested with *Staphylococcus aureus* (MRSA). These data show that the presence of the manganese complex in the irradiated composition conferred greater immune response in the treated mice.

The approach was also successfully tested on a pathogenic *Staphylococcus aureus* strain (FIG. 6). In contrast, viruses and bacteria exposed to supralethal doses of IR without the $Mn^{2+}$ complexes resulted in substantial loss of viral epitope integrity and loss in immunogenicity.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents, and patent applications referred to in this application are herein incorporated by reference in their entirety.

What is claimed is:

1. A method of producing a replication-deficient microorganism, the method comprising
 a) culturing, harvesting, and/or suspending a viable microorganism in an aqueous environment comprising a radiation-protective composition, the composition comprising divalent manganese, orthophosphate and (i) a collection of amino acids consisting of Aspartate, Glutamate, Histidine, Glycine, Threonine, Alanine, Valine, Methionine, Leucine, and Lysine, or (ii) a peptide of about 25 residues in length or less, with the peptide consisting of amino acids Aspartate, Glutamate, Histidine, Glycine, Threonine, Alanine, Valine, Methionine, Leucine, and Lysine,
 b) irradiating the microorganism in the radiation-protective composition with a dose of ionizing radiation sufficient to render the microorganism replication-deficient.

2. The method of claim 1, wherein the radiation is selected from the group consisting of ultraviolet radiation, alpha radiation, beta radiation, gamma radiation, X-ray radiation and neutron radiation.

3. The method claim 1, wherein the composition further comprises at least one nucleoside selected from the group consisting of adenosine, uridine, β-pseudouridine, inosine, and mixtures thereof.

4. The method of claim 3, wherein the at least one nucleoside is adenosine or uridine.

5. The method of claim 4, wherein the concentration of the at least one nucleoside is from about 1 mM to about 15 mM.

6. The method of claim 1, wherein concentration of the divalent manganese is from about 1 mM to about 12.5 mM.

7. The method of claim 1, wherein the divalent manganese is in a form selected from the group consisting of MnCl$_2$ and manganous phosphate.

8. The method of claim 1, wherein the composition further comprises an ultrafiltrate from *Deinococcus radiodurans*.

9. The method of claim 1, wherein the dose of radiation is at least about 10 kGy.

10. The method of claim 1, wherein the microorganism is a bacterium.

11. The method of claim 10, wherein the bacterium is *Staphylococcus*.

12. The method of claim 11, wherein the *Staphylococcus* is *Staphylococcus aureus*.

13. The method of claim 1, wherein the peptide comprises the amino acid sequence of SEQ ID NO:1.

14. The method of claim 1, wherein the microorganism is a virus.

15. A method of producing a replication-deficient microorganism, the method comprising
 a) culturing, harvesting, and/or suspending a viable microorganism in an aqueous environment comprising a radiation-protective composition, the composition comprising divalent manganese at a concentration from about 1 mM to about 12.5 mM, orthophosphate, a peptide of about 25 residues in length or less, with the peptide consisting of amino acids Aspartate, Glutamate, Histidine, Glycine, Threonine, Alanine, Valine, Methionine, Leucine, and Lysine, and at least one nucleoside selected from the group consisting of adenosine, uridine, 3-pseudouridine, and inosine;
 b) irradiating the microorganism in the radiation-protective composition with a dose of ionizing radiation sufficient to render the microorganism replication-deficient.

16. The method of claim 15, wherein the peptide comprises the amino acid sequence of SEQ ID NO:1.

17. The method of claim 15, wherein the microorganism is a virus.

18. The method of claim 15, wherein the radiation is selected from the group consisting of ultraviolet radiation, alpha radiation, beta radiation, gamma radiation, X-ray radiation and neutron radiation.

19. The method of claim 15, wherein the microorganism is a bacterium.

20. The method of claim 19, wherein the bacterium is *Staphylococcus*.

21. The method of claim 20, wherein the *Staphylococcus* is *Staphylococcus aureus*.

22. A method of producing a replication-deficient microorganism, the method comprising
 a) culturing, harvesting, and/or suspending a viable microorganism in an aqueous environment comprising a radiation-protective composition, the composition comprising divalent manganese, orthophosphate and (i) a collection of amino acids consisting of asparagine, glutamine, serine, histidine, glycine, threonine, arginine, tyrosine, methionine, phenylalanine, isoleucine, lysine, ornithine, leucine, valine and alanine or (ii) a peptide of about 25 residues in length or less, with the peptide consisting of amino acids aspartate, glutamate, serine, histidine, glycine, threonine, arginine, tyrosine, methionine, phenylalanine, isoleucine, lysine, ornithine, leucine, valine and alanine,
 b) irradiating the microorganism in the radiation-protective composition with a dose of ionizing radiation sufficient to render the microorganism replication-deficient.

23. The method of claim 22, wherein the radiation is selected from the group consisting of ultraviolet radiation, alpha radiation, beta radiation, gamma radiation, X-ray radiation and neutron radiation.

24. The method claim 22, wherein the composition further comprises at least one nucleoside selected from the group consisting of adenosine, uridine, β-pseudouridine, inosine, and mixtures thereof.

25. The method of claim 24, wherein the at least one nucleoside is adenosine or uridine.

26. The method of claim 25, wherein the concentration of the at least one nucleoside is from about 1 mM to about 15 mM.

27. The method of claim 22, wherein concentration of the divalent manganese is from about 1 mM to about 12.5 mM.

28. The method of claim 22, wherein the divalent manganese is in a form selected from the group consisting of MnCl2 and manganous phosphate.

29. The method of claim 22, wherein the composition further comprises an ultrafiltrate from *Deinococcus radiodurans*.

30. The method of claim 22, wherein the dose of radiation is at least about 10 kGy.

31. The method of claim 22, wherein the microorganism is a bacterium.

32. The method of claim 31, wherein the bacterium is *Staphylococcus*.

33. The method of claim 32, wherein the *Staphylococcus* is *Staphylococcus aureus*.

34. A method of producing a replication-deficient microorganism, the method comprising
   a) culturing, harvesting, and/or suspending a viable microorganism in an aqueous environment comprising a radiation-protective composition, the composition comprising divalent manganese at a concentration from about 1 mM to about 12.5 mM, orthophosphate, a peptide of about 25 residues in length or less, with the peptide consisting of amino acids aspartate, glutamate, serine, histidine, glycine, threonine, arginine, tyrosine, methionine, phenylalanine, isoleucine, lysine, ornithine, leucine, valine and alanine, and at least one nucleoside selected from the group consisting of adenosine, uridine, 3-pseudouridine, and inosine;
   b) irradiating the microorganism in the radiation-protective composition with a dose of ionizing radiation sufficient to render the microorganism replication-deficient.

35. The method of claim 34, wherein the microorganism is a virus.

36. The method of claim 34, wherein the radiation is selected from the group consisting of ultraviolet radiation, alpha radiation, beta radiation, gamma radiation, X-ray radiation and neutron radiation.

37. The method of claim 34, wherein the microorganism is a bacterium.

38. The method of claim 37, wherein the bacterium is *Staphylococcus*.

39. The method of claim 38, wherein the *Staphylococcus* is *Staphylococcus aureus*.

* * * * *

SEQUENCE LISTING

<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Consensus amino acid sequence of hundreds of
      peptides purified from D. radiourans

<400> SEQUENCE: 1

Asp Glu His Gly Thr Ala Val Met Leu Lys
1               5                   10